United States Patent
Ash et al.

(10) Patent No.: US 7,820,448 B2
(45) Date of Patent: *Oct. 26, 2010

(54) WASTE MATERIALS SAMPLING, ASSAYING FOR DESIRED COMPONENTS OR METALS, AND REFINING

(75) Inventors: Peter William Ash, Reading (GB); Piers Scott Grumett, Brussels (BE); Brian Harrison, Bedfordshire (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/211,387

(22) Filed: Sep. 16, 2008

(65) Prior Publication Data

US 2009/0007727 A1    Jan. 8, 2009

Related U.S. Application Data

(63) Continuation of application No. 10/494,405, filed as application No. PCT/GB02/04724 on Oct. 18, 2002, now Pat. No. 7,439,070.

(30) Foreign Application Priority Data

Nov. 2, 2001    (GB)    .................................. 0126346.6

(51) Int. Cl.
*G01N 33/20*    (2006.01)
*G01N 1/10*    (2006.01)

(52) U.S. Cl. .............................. 436/80; 422/62; 436/52; 436/73; 436/84; 436/171; 436/174; 436/175; 436/179

(58) Field of Classification Search .................. 422/62; 436/26, 43, 52, 73, 80, 84, 171, 174–175, 436/179
See application file for complete search history.

(56) References Cited

U.S. PATENT DOCUMENTS

| | | | |
|---|---|---|---|
| 3,953,306 A | 4/1976 | Lancy | |
| 4,545,957 A | 10/1985 | Vanhumbeeck et al. | |
| 4,720,998 A | 1/1988 | Hogue | |
| 5,011,596 A * | 4/1991 | Shaw | ......................... 209/167 |
| 5,038,623 A | 8/1991 | Zeh | |
| 5,114,902 A | 5/1992 | Schwarz et al. | |

(Continued)

FOREIGN PATENT DOCUMENTS

EP    0 165 801 A2    12/1985

(Continued)

OTHER PUBLICATIONS

Mousa, A. A. et al, Resources, Conservation and Recycling 1995, 15, 95-110.*

(Continued)

*Primary Examiner*—Arlen Soderquist
(74) *Attorney, Agent, or Firm*—RatnerPrestia

(57) ABSTRACT

A bulk sample is fed with a liquid into a mixing tank (1) where it is stirred to form a dispersion. A proportion of the dispersion is recycled from the bottom of the tank through a line to the top of the tank so that at least the dispersion in the recycle loop (3) is substantially homogeneous, and a representative sample of the dispersion is taken from the recycle loop, e.g. using a slurry sampler (5).

18 Claims, 2 Drawing Sheets

U.S. PATENT DOCUMENTS

| | | | |
|---|---|---|---|
| 5,227,010 A | 7/1993 | Lubert et al. | |
| 5,496,392 A * | 3/1996 | Sims et al. | 75/414 |
| 5,560,823 A | 10/1996 | Whiting | |
| 5,688,401 A | 11/1997 | Bober et al. | |
| 5,766,478 A | 6/1998 | Smith et al. | |
| 6,056,790 A | 5/2000 | Clark et al. | |
| 6,145,468 A | 11/2000 | Woog | |
| 7,122,167 B2 * | 10/2006 | Collard et al. | 423/592.1 |
| 7,335,618 B2 | 2/2008 | Koyama et al. | |
| 7,439,070 B2 * | 10/2008 | Ash et al. | 436/80 |

FOREIGN PATENT DOCUMENTS

| | | |
|---|---|---|
| EP | 0 561 078 A2 | 9/1993 |
| EP | 0 931 766 A2 | 7/1999 |
| NL | 7006663 | 11/1971 |
| WO | WO-00/68664 | 11/2000 |
| WO | WO-01/83834 A1 | 11/2001 |

OTHER PUBLICATIONS

Lai, Y. D. et al, Journal of Hazardous Materials 1997, 53, 213-224.*

Yoo, J. S., Catalysis Today 1998, 44, 27-46.*

* cited by examiner

WASTE MATERIALS SAMPLING, ASSAYING FOR DESIRED COMPONENTS OR METALS, AND REFINING

CROSS-REFERENCE TO RELATED APPLICATIONS

This application is a continuation application of U.S. patent application Ser. No. 10/494,405, filed Oct. 26, 2004, which is the U.S. National Phase application of PCT International Application No. PCT/GB02/04724, filed Oct. 18, 2002, and claims priority of British Application No. 0126346.6, filed Nov. 2, 2001, all of which are incorporated herein by reference.

FIELD OF THE INVENTION

The present invention concerns improvements in materials handling, more especially it concerns improvements in the sampling, and eventual analysis or assay, of variable feedstocks.

BACKGROUND OF THE INVENTION

Many processes involve the sampling of bulk variable feedstocks, and this has especial importance where the feedstock contains one or more high value components. For example, in the recycle and refining of waste catalysts, or other wastes containing materials such as the platinum group metals, silver and gold, the refining organisation needs to determine levels of such metals in the bulk material to assess the value of metals to be credited to the owner of the bulk material. There is a need for improved sampling methods and, accordingly, for improved metal assays.

SUMMARY OF THE INVENTION

The bulk materials acting as feedstocks in the present invention may be in any non-gaseous form, for example liquid, such as waste homogeneous catalyst, solid or slurry. If the feedstock is a solid, such as a filter cake or other solid form, it is necessary to break up the solid, by for example crushing or milling so that the bulk is dispersible. Desirably, the particle size of solids is less than 500 µm, preferably less than 100 µm, bearing in mind the need to obtain suspension as a homogeneous slurry.

The present invention accordingly provides a method of refining comprising receiving a bulk sample of unknown composition, sampling the bulk sample to yield a reduced volume sample, assaying said reduced volume sample for one or more desired components, calculating the content of one or more desired components in the bulk sample, and passing the remaining bulk sample to a refining process; wherein sampling of the bulk sample comprises dispersing the bulk sample in a liquid, stirring the resulting dispersion in a mixing tank, continuously withdrawing from the bottom section of the tank a portion of the dispersion and recycling it via a recycle loop to the upper portion of the tank such that a substantially homogeneous dispersion is obtained in at least the recycle loop, and taking a representative sample of dispersion from the recycle loop. If necessary, the reduced volume sample may be subsequently sub-divided and representative sub-division samples are assayed or analysed for key components in conventional manner.

BRIEF DESCRIPTION OF THE DRAWINGS

The present invention will now be described by way of example only and with reference to the accompanying drawings in which.

DETAILED DESCRIPTION OF THE INVENTION

Figure 1:
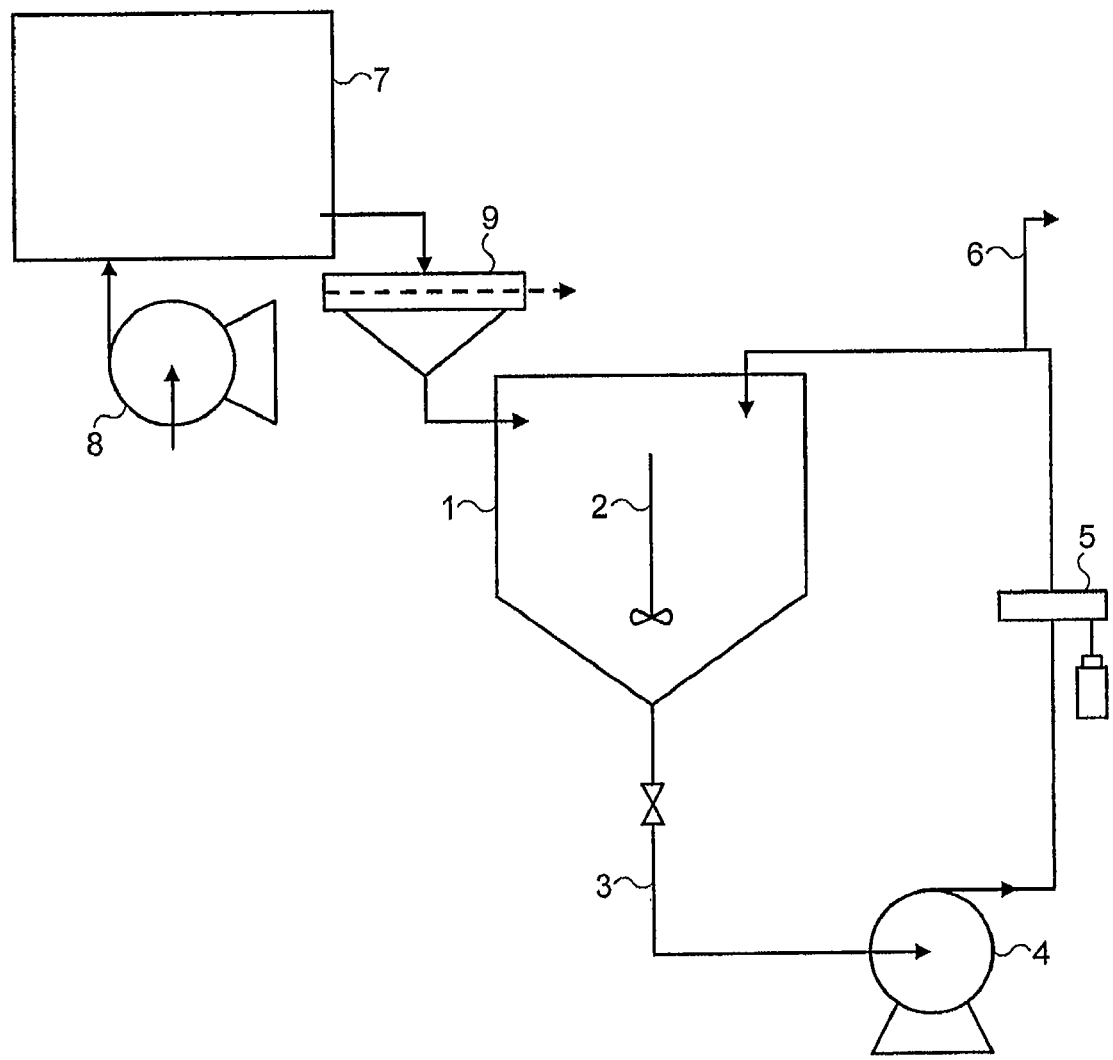
FIG. 1 shows a schematic representation of apparatus for carrying out sampling according to the invention; and, FIG. 2 is a graph comparing metal values for a range of samples evaluated using the method of the present invention with those obtained using conventional pyrolysis.

Preferably, the refining process is a supercritical water oxidation process as described in WO 01/83834. For technical reasons, conventional refining techniques do not sample and assay the bulk sample, but only sample and assay after one or more preliminary concentration or refining steps. Accordingly, the present invention represents a significant departure from the state of the art, and is believed to offer advantages in speed of processing, and hence significantly reduce the cost of financing "work in progress".

The method of sampling according to the invention desirably uses a conical-ended stirred mixing tank, fitted with a pipe at the apex of the cone. Other tank shapes may, however, be used, for example a hemispherical, frusto-conical or similar section base. The recycle of dispersion is to the upper section of the tank, and may be made to any one or more points in said upper section. Conveniently, a single recycle point is approximately half-way along a radius of the tank.

Suitable mixing speeds, impeller shapes, recycle line diameters and recycle rates may vary according to the volume of the mixing tank and volume of the sample dispersion, and may be established by routine experiment. The aim is, of course, to ensure that the representative sample taken from the recycle loop is truly representative and this is essentially achieved by ensuring that the dispersion is homogenised.

Particularly preferred bulk sample feedstocks are spent catalysts, especially those comprising a platinum group metal carried on a carbon support. Such spent catalysts generally contain considerable quantities of organic solvent. However, since these are often regarded as wastes, they may be contaminated with a variety of organic (e.g. paper, cloth etc.) or inorganic (e.g. nuts and bolts etc.) matter. Such contaminating matter is desirably screened out.

Suitable liquid or slurry samplers are commercially available for use in the recycle loop. The volume taken is not especially important.

The methods used for assay or further analysis are conventional and form no part of this invention. Similarly, refining methods may be conventional or the supercritical water method of WO 01/83834.

Depending upon the nature of the bulk sample and especially the nature of solvents or residues associated with the values in the bulk sample, an additive to improve dispersion in the liquid may be required. The liquid is advantageously water, and conventional and commercially available surfactants may be used if the bulk sample is essentially non-polar. Initial tests on bulk samples which have a polar character indicate that certain surfactants, e.g. "Quadralene"™ (used for glassware washing machines) may be advantageously used.

Suitable concentrations of bulk sample in the liquid are from 10-15 wt %. Conveniently, the bulk sample, crushed or milled if necessary, is added, together with an appropriate surfactant, to the tank already charged with water, mixing is begun and the recycle initiated.

With reference to FIG. 1, apparatus for carrying out the invention includes a mixing tank, 1. In proving trials, a steel tank of 600 liter capacity, with a conical bottom, has been used. A conventional axial impeller, 2, is fitted in tank 1, to mix the contents. A recycle line, 3, of 19 mm internal diameter is attached to the conical base of tank 1.

The recycle line is connected to a pump, 4, before being returned to the upper section of tank 1. The pump has been operated at 4400 l/hr. Fitted downstream of the pump is a commercial liquid/slurry sampler "Isolock"™ 5, which collects a sample volume of 500 ml.

The recycle line may include a line, 6, to allow the contents of the tank to be emptied or further processed.

The charge of bulk sample is conveniently received in a bulk container, 7, fitted with a pump, 8, for water, wash water and/or surfactant. The bulk sample is fed to a screen, 9, to remove gross contaminants; a screen size of 3-10 mm size is generally appropriate for spent carbon-based catalyst.

The sample is suitably passed to an assay laboratory, where it is resuspended and kept agitated. Sub-samples may be taken by using tube sampling. It is generally good practice to take a number of samples, some of which may be retained as a reference sample, to minimise the opportunity for process variability.

For example, where the bulk sample consists essentially of spent carbon-supported catalyst with organic solvent, it is preferred to oxidise all organic/carbonaceous material to $CO_2$, using a mixture of sulphuric and nitric acids. The residual precious metal can then be dissolved in a pre-set volume of aqua regia and analysed, for example using Inductively Coupled Plasma Emission Spectroscopy against standard solutions of known platinum group metal content.

EXAMPLE

Figure 2:
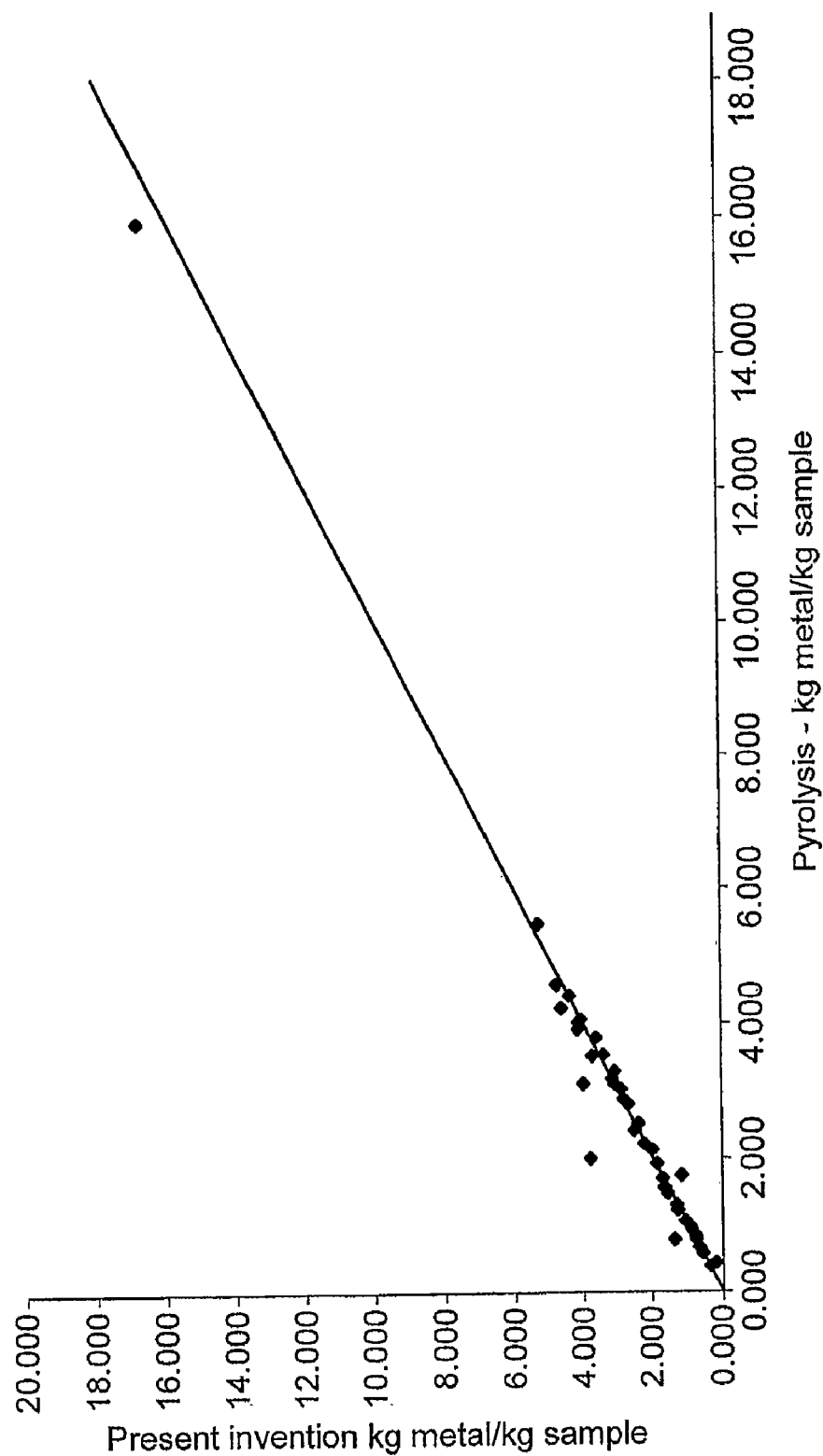

Fifty-one catalyst samples were evaluated using the method of the invention. The samples were sourced from a wide range of used and unused materials with a range of physical properties and impurities. Results are shown in Table 1. Recovery is measured as the ratio (expressed as a percentage) between the amount of metal evaluated in each sample using the method of the invention and that evaluated by conventional pyrolysis. Excellent agreement was found between the two methods indicating that method of the invention provides an accurate and reliable measure of total metal content. The results of Table 1 are illustrated graphically in FIG. 2, with a line of unit gradient for reference.

It will be appreciated by the skilled person, that the method and apparatus as described may be varied in many ways. The invention includes all novel items and novel combinations and equivalents thereof. The skilled person may readily adapt the description herein in order to optimise the invention for particular circumstances.

TABLE 1

| Sample No. | Recovery/% |
| --- | --- |
| 1 | 100.6 |
| 2 | 100.7 |
| 3 | 96.3 |
| 4 | 98.5 |
| 5 | 103.5 |
| 6 | 180.4 |
| 7 | 128.6 |
| 8 | 99.5 |
| 9 | 94.2 |
| 10 | 106.7 |
| 11 | 101.0 |
| 12 | 96.7 |
| 13 | 94.5 |
| 14 | 94.7 |
| 15 | 99.8 |
| 16 | 96.3 |
| 17 | 101.4 |
| 18 | 102.0 |
| 19 | 96.6 |
| 20 | 103.6 |
| 21 | 94.0 |
| 22 | 100.0 |
| 23 | 94.9 |
| 24 | 92.4 |
| 25 | 191.1 |
| 26 | 98.6 |
| 27 | 95.0 |
| 28 | 103.2 |
| 29 | 92.6 |
| 30 | 67.6 |
| 31 | 99.0 |
| 32 | 105.2 |
| 33 | 104.5 |
| 34 | 39.9 |
| 35 | 92.3 |
| 36 | 100.7 |
| 37 | 96.2 |
| 38 | 95.6 |
| 39 | 104.7 |
| 40 | 105.7 |
| 41 | 106.7 |
| 42 | 96.7 |
| 43 | 104.9 |
| 44 | 101.8 |
| 45 | 94.3 |
| 46 | 109.1 |
| 47 | 103.3 |
| 48 | 105.3 |
| 49 | 118.4 |
| 50 | 92.1 |
| 51 | 97.0 |

What is claimed:

1. A method of refining, the method comprising receiving a bulk sample of unknown composition, sampling the bulk sample to yield a reduced volume sample, assaying said reduced volume sample for one or more desired components, calculating the content of one or more desired components in the bulk sample, and passing the remaining bulk sample to a refining process; wherein sampling of the bulk sample comprises dispersing the bulk sample in a liquid, stirring the resulting dispersion in a mixing tank, continuously withdrawing from the bottom section of the tank a portion of the dispersion and recycling it via a recycle loop to the upper portion of the tank such that a substantially homogeneous dispersion is obtained in at least the recycle loop, and taking a representative sample of dispersion from the recycle loop.

2. A method according to claim 1, wherein the bulk sample is a spent catalyst.

3. A method according to claim 2, wherein the spent catalyst is a platinum group metal on carbon catalyst.

4. A method according to claim 1, wherein the liquid is water.

5. A method according to claim 1, where a surfactant is added to the liquid to facilitate dispersion.

6. A method according to claim 1, wherein the sample is a solid having particle size of less than 500 μm.

7. A method according to claim 1, wherein the refining process is a supercritical water oxidation process.

8. A method according to claim 1, where a surfactant is added to the sample to facilitate dispersion.

9. A method according to claim 1, wherein the sample is a solid having particle size of less than 100 μm.

10. A method according to claim 1, wherein the concentration of the bulk sample in the liquid is between 10 and 15 wt %.

11. A method of refining a metal-containing waste containing at least one metal selected from the group consisting of platinum group metals, silver and gold and combinations thereof to recover the metal therefrom, which method comprising receiving a bulk sample of the waste of unknown composition, dispersing the bulk sample in water to form a bulk sample dispersion, stirring the bulk sample dispersion in a mixing tank, continuously withdrawing from the bottom section of the tank a portion of the bulk sample dispersion and recycling it via a recycle loop to the upper portion of the tank such that a substantially homogeneous dispersion is obtained in at least the recycle loop, taking a representative sample of the bulk sample dispersion from the recycle loop to yield a reduced volume sample, assaying the reduced volume sample for the metal, calculating the content of the metal in the remaining bulk sample dispersion, and recovering the metal from the remaining bulk sample dispersion in a supercritical water oxidation process.

12. A method according to claim 11, wherein the bulk sample is a spent catalyst.

13. A method according to claim 12, wherein the spent catalyst is a platinum group metal on carbon catalyst.

14. A method according to claim 11, where a surfactant is added to the water to facilitate dispersion.

15. A method according to claim 11, wherein the sample is a solid having particle size of less than 500 μm.

16. A method according to claim 11, where a surfactant is added to the sample to facilitate dispersion.

17. A method according to claim 11, wherein the sample is a solid having particle size of less than 100 μm.

18. A method according to claim 11, wherein the concentration of the bulk sample in the water is between 10 and 15 wt %.

\* \* \* \* \*